(12) United States Patent
Macrelli et al.

(10) Patent No.: US 11,988,600 B2
(45) Date of Patent: May 21, 2024

(54) GAS SENSOR MEMS STRUCTURES AND METHODS OF FABRICATION THEREOF

(71) Applicants: National University of Singapore, Singapore (SG); The Regents of the University of California, Oakland, CA (US)

(72) Inventors: Enrico Macrelli, Singapore (SG); Massimo Bruno Cristiano Alioto, Singapore (SG); Chengkuo Lee, Singapore (SG); Costas John Spanos, Berkeley, CA (US); You Qian, Singapore (SG)

(73) Assignees: National University of Singapore, Singapore (SG); The Regents of the University of California, Oakland, CA (US)

( * ) Notice: Subject to any disclaimer, the term of this patent is extended or adjusted under 35 U.S.C. 154(b) by 1381 days.

(21) Appl. No.: 16/467,091

(22) PCT Filed: Dec. 8, 2017

(86) PCT No.: PCT/SG2017/050609
§ 371 (c)(1),
(2) Date: Jun. 6, 2019

(87) PCT Pub. No.: WO2018/106193
PCT Pub. Date: Jun. 14, 2018

(65) Prior Publication Data
US 2019/0360924 A1    Nov. 28, 2019

Related U.S. Application Data

(60) Provisional application No. 62/432,180, filed on Dec. 9, 2016.

(30) Foreign Application Priority Data
Dec. 9, 2016    (SG) .......................... 10201610369X

(51) Int. Cl.
*G01N 33/00*    (2006.01)
*B81B 3/00*    (2006.01)
(Continued)

(52) U.S. Cl.
CPC ....... *G01N 21/3504* (2013.01); *B81B 3/0083* (2013.01); *B81C 1/00246* (2013.01);
(Continued)

(58) Field of Classification Search
CPC ........... G01N 21/3504; G01N 33/0031; G01N 2201/02; B81B 3/0083; B81B 2203/0315;
(Continued)

(56) References Cited

U.S. PATENT DOCUMENTS 3,793,525 A    2/1974    Burch et al.
3,811,776 A    5/1974    Blau, Jr.
(Continued)

FOREIGN PATENT DOCUMENTS

CN    200982950 Y    11/2007
CN    101554987 A    10/2009
(Continued)

OTHER PUBLICATIONS

Chinese Patent Office Action for Application No. 201780083524.3 dated Apr. 6, 2022 (50 pages, including English translation).
(Continued)

*Primary Examiner* — Freddie Kirkland, III
(74) *Attorney, Agent, or Firm* — Michael Best & Friedrich LLP

(57) ABSTRACT

A gas sensor, a method of manufacturing a gas sensor, a method for fabricating a micro electro-mechanical system
(Continued)

(MEMS) die for a heater or thermopile, and a micro electro-mechanical system (MEMS) die for a heater or thermopile. The gas sensor comprises a first micro electro-mechanical system (MEMS) die comprising a light source; a second MEMS die comprising a light detector; a sample chamber disposes in an optical path between the light source and the light detector; and a holder substrate; wherein the first and second MEMS dies are disposed on the holder substrate in a vertical orientation relative to the holder.

8 Claims, 11 Drawing Sheets

(51) Int. Cl.
  *B81C 1/00* (2006.01)
  *G01N 21/3504* (2014.01)
  *H10N 10/01* (2023.01)
  *H10N 10/80* (2023.01)
(52) U.S. Cl.
  CPC ......... *G01N 33/0031* (2013.01); *H10N 10/01* (2023.02); *H10N 10/80* (2023.02); *B81B 2203/0315* (2013.01); *B81B 2207/07* (2013.01); *B81C 2203/0714* (2013.01); *G01N 2201/02* (2013.01)
(58) Field of Classification Search
  CPC ............ B81B 2207/07; B81C 1/00246; B81C 2203/0714; H10N 10/01; H10N 10/80
  See application file for complete search history.

(56) References Cited

U.S. PATENT DOCUMENTS

| | | |
|---|---|---|
| 4,578,762 A | 3/1986 | Wong |
| 4,694,173 A | 9/1987 | Wong |
| 5,163,332 A | 11/1992 | Wong |
| 5,222,389 A | 6/1993 | Wong |
| 5,341,214 A | 8/1994 | Wong |
| 5,347,474 A | 9/1994 | Wong |
| 5,444,249 A | 8/1995 | Wong |
| 5,453,621 A | 9/1995 | Wong |
| 5,502,308 A | 3/1996 | Wong |
| 5,747,808 A | 5/1998 | Wong |
| 5,834,777 A | 11/1998 | Wong |
| 6,237,575 B1 | 5/2001 | Lampert et al. |
| 8,143,581 B2 | 3/2012 | Wong |
| 8,624,380 B2 | 1/2014 | Xue et al. |
| 8,836,132 B2 | 9/2014 | Xue |
| 9,171,885 B2 * | 10/2015 | Nam .................. G01J 5/12 |
| 10,161,857 B2 * | 12/2018 | Nomoto .............. G02B 1/11 |
| 10,309,895 B2 * | 6/2019 | Fujisawa ............ G01N 21/3504 |
| 11,193,885 B2 * | 12/2021 | Tortschanoff ...... G01N 33/0027 |
| 11,237,098 B2 * | 2/2022 | Tumpold .............. B81B 7/02 |
| 2010/0032788 A1 * | 2/2010 | Ulbrich ................ G01J 5/023 |
| | | 257/E31.093 |
| 2014/0246749 A1 | 9/2014 | Nam et al. |
| 2014/0248735 A1 | 9/2014 | Purkl et al. |
| 2016/0016789 A1 | 1/2016 | Yu et al. |
| 2016/0240762 A1 | 8/2016 | Carr |
| 2017/0023466 A1 * | 1/2017 | Nomoto ............ G01N 21/6428 |
| 2018/0374981 A1 * | 12/2018 | Carr .................... H01L 31/147 |
| 2020/0072739 A1 * | 3/2020 | Sasayama ............ G02B 5/281 |
| 2020/0309678 A1 * | 10/2020 | Tumpold ............ G01N 27/124 |
| 2021/0302308 A1 * | 9/2021 | Segovia Fernandez ................... |
| | | G01N 21/554 |

FOREIGN PATENT DOCUMENTS

| | | |
|---|---|---|
| CN | 104266974 A | 1/2015 |
| CN | 104535197 A | 4/2015 |
| CN | 105486654 A | 4/2016 |
| WO | 2017088071 A1 | 6/2017 |

OTHER PUBLICATIONS

International Search Report and Written Opinion Application No. PCT/SG2017/050609, dated Mar. 15, 2018 (15 pages).

Chowdhury, M.F. et al, "MEMS Infrared Emitter and Detector for Capnography Apoplications," Procedia Engineering, Sep. 7, 2016, vol. 168, pp. 1204-1207.

Chinese Patent Office Action for Related Application No. 201780083524.3 dated Oct. 10, 2022 (49 pages, including an English translation).

\* cited by examiner

GAS SENSOR MEMS STRUCTURES AND METHODS OF FABRICATION THEREOF

FIELD OF INVENTION

The present Invention, in one aspect, relates broadly to the field of gas sensors, and specifically relates to light-emission and -detection based gas sensors such as non-dispersive infrared (NDIR) gas sensors to determine the concentration of a particular gas present in a chamber by sensing the absorption of infrared radiation through the gas.

The present Invention, in another aspect, relates broadly to the field of infrared sources and detectors such as microheater source and thermopile detector, in particular aiming to enhance the performance of the devices, as well as increase the fabrication yield of the devices.

BACKGROUND

Any mention and/or discussion of prior art throughout the specification should not be considered, in any way, as an admission that this prior art is well known or forms part of common general knowledge in the field.

Light-emission and -detection based gas sensors such as the non-dispersive infrared (NDIR) gas sensors have long been considered as one of the best methods for gas measurement. NDIR gas sensors exploit the fact that various gases show large absorption at specific wavelengths in the infrared radiation spectrum. The term non-dispersive indicates the type of device incorporating the NDIR technique, usually with a narrow bandpass filter to select radiation in a particular wavelength band from a broadband infrared source. When compared to other gas detection methods such as electrochemical fuel cells, tin oxide ($SnO_2$) sensors, metal oxide semiconductor (MOS) sensors, catalytic sensors, photo-ionization detector (PID), flame-ionization detector (FID), and thermal conductivity sensors, which are all referred to as interactive gas detectors, NDIR gas sensors are highly specific, sensitive, fast responding, relatively stable over time, reliable, and easy to maintain.

In the past, NDIR gas sensors typically comprise: an infrared radiation source with a motor-driven mechanical chopper to modulate the source, a pump to push gas through a sample chamber, a narrow bandpass filter, a sensitive infrared detector, and infrared optics and windows to focus the infrared energy from the source onto the detector. Even if the NDIR gas measurement technique is one of the best practices that has been developed, it has not appreciated wide application because of its complexity and high cost as compared to other gas detection methods.

Ever since the NDIR technique of gas measurement was first introduced in the mid 1950's, a large number of improved measurement techniques based upon the NDIR principle for gas detection have been proposed and successfully demonstrated. In 1974 Burch et al. (U.S. Pat. No. 3,793,525) and Blau et al. (U.S. Pat. No. 3,811,776) advanced a dual beam technique for NDIR gas measurement by taking advantage of the principle of nonlinear absorption for some strongly absorbing gases such as carbon dioxide ($CO_2$) to create a reference channel. Shortly afterwards, this dual beam NDIR gas sensor technique was greatly simplified with the use of two interposed spectral filters (one absorbing and one neutral) to build a sample and a reference detector channel. Subsequent NDIR gas sensors with this technique have appreciated good performance. In U.S. Pat. No. 4,578,762 (1986) Wong advanced a self-calibrating NDIR $CO_2$ analyzer using a novel two-wheel chopper and mirror arrangement. Another improved type of such gas analyzer is described in U.S. Pat. No. 4,694,173 (1987) by Wong. This gas sensor has no moving parts for achieving the interposition of spectral filters to make both a sample and reference detector channel as in the NDIR gas sensors described previously.

In an attempt to reduce the cost and simplify the implementation of the NDIR method, in U.S. Pat. No. 5,163,332 (1992), Wong proposed the waveguide diffusion sample chamber concept to make NDIR gas sensors more compact, rough and low-cost while still keeping their superior performance characteristics. The waveguide diffusion sample chamber uses an elongated hollow tube having an inner reflective surface that permits the tube to function as a light-pipe to transmit radiation from a source to a detector through the sample gas. A plurality of apertures in the wall of the non-porous hollow tube let the sample gas to enter and exit freely under environmental pressure. Particles of smoke and dust are kept out of the chamber by use of a semi permeable membrane that extents the apertures, whereas condensation of the sample gas (or air) can be prevented by heating the sample chamber to a temperature above the dew point of the gas (or air). This concept has been broadly adopted in the design of today's NDIR gas sensors, particularly in low-cost and high volume sorts.

In the following years, Wong has continued to refine and improve low-cost NDIR gas sensors as evidenced by the issuance of U.S. Pat. No. 5,222,389 (June 1993), U.S. Pat. No. 5,341,214 (August 1994), U.S. Pat. No. 5,347,474 (September 1994), U.S. Pat. No. 5,453,621 (September 1995), U.S. Pat. No. 5,502,308 (March 1996), U.S. Pat. No. 5,747,808 (May 1998), U.S. Pat. No. 5,834,777 (November 1998) and U.S. Pat. No. 6,237,575 (May 2001). Until recently, efforts to reduce the cost of an NDIR gas sensor have been focused mainly in developing lower cost infrared components, improving sensor structure and optical designs, and simplification of electronic signal processing circuits. Up to now, the most widespread NDIR gas sensor is a dual beam device having a signal and a reference beam realized with a single infrared source and two separate infrared detectors, each with a different bandpass filter. The signal filter contains a narrow spectral bandpass tuned to the absorption radiation of the gas. Thus the presence of the gas of interest will modulate the signal beam. Besides, the reference filter encloses a narrow spectral bandpass that is irrelevant to the gas in question and also to all the common gases present in the atmosphere. Hence, the reference beam acts as a reference for the detection of the gas species over time.

Nowadays the dual beam technique works well for many applications, especially for the detection of relatively low concentration of $CO_2$ gas (400-2000 ppm) for heating, ventilation and air conditioning (HVAC) systems and indoor air quality (IAQ) applications. However, the cost reduction for the sensor is limited by the expensive detector package which contains two detectors each furnished with a different filter. Additionally, the dual beam NDIR gas sensor still has a number of limitations that require special actions in order to render the sensor reliable and stable for use over time. These limitations include the aging of the infrared source which might cause the spatial distribution of infrared radiation reaching the detectors to change, and the non-uniform aging of the inner reflective surfaces of the sample chamber which might affect the spatial distribution of the imposing radiation at the detector assembly. Finally, the different aging characteristics for the two filters are a limitation, each being made via different processes and the resulting potential different aging characteristics for the two detectors.

All of the NDIR gas sensors previously described perform well and have contributed effectively to the overall technical progress in the field of gas analysis during the past two decades. They have been widely accepted in both medical and industrial communities. However, regardless of their success over the years, there still remain several characteristics that need to be significantly improved in order to further extend the useful applications of these devices. By far, the first drawback of today's gas sensors, inclusive of NDIR gas sensors, is the sensor output stability over time, i.e. drift over time, for instance due to the aging of the infrared source by heating up many times in a lifecycle to deliver the IR energy. This will result in a change of its spectral output intensities. This means that every gas sensor requires recalibration once every three months to a year in order to remain accurate over time. For instance, without an output stable $CO_2$ controller, the implementation and practice of demand-controlled ventilation (DCV) strategy in office and commercial buildings to save energy would be very inconvenient. The second drawback for today's gas sensors, regardless of their operational principle, is the output dependence as a function of the temperature of the environment, i.e. drift over temperature, in which the sensor is located. This problem is generally resolved by specifying the output correction per degree of temperature change with respect to the output at a standard temperature. However, these output temperature corrections typically limit the use of these sensors outdoors.

The aforementioned NDIR gas sensor performance deficits, have been recently addressed in U.S. Pat. No. 8,143,581 (2009) by Wong with the absorption biased NDIR methodology. This method takes advantage of the fact that, assuming a dual-channel device, the output of the sensor taken as the ratio of the signal output over the reference output can always be kept constant or unchanged over time except when the gas of interest is present in the sample chamber. Hence, both the signal and the reference channel must be built with exactly the same spectral narrow bandpass filter. In order to differentiate between the signal and the reference channel outputs in the presence of the gas of interest, an absorption bias is designed between the two channels via the use of different sample chamber path lengths for the two channels. The fact that both detection channels have the same narrow bandpass filter and they receive radiation from the same single infrared source has shown that they are all affected in the same way to first order when there are spectral changes caused by temperature variations in the sample chamber and/or by the short or long-term operational changes (e.g. aging) of the infrared source.

Another recent approach to address the sensor output drift over time is related to the combination of all sensors in a building into wireless sensor networks (WSNs). These sensors can actually interact and work with one another in an efficient way with self-commissioning, self-tuning, self-diagnostic and correction, and even self-configuring features. By so doing the energy requirement for buildings can be reduced while the comfort level and safety for occupants in the buildings can also be greatly increased. Other approaches include the use of feedback circuitry to control and keep constant the infrared source temperature by adjusting the voltage delivered to the source. Other recent tactics comprise the use of post processing algorithms capable to compensate the environmental variations by measuring the sample chamber temperature, pressure, and eventually relative humidity (RH) through sensors.

Also, two other important performance characteristics, namely miniaturization and lowest unit cost, have still not been addressed. Electrochemical gas sensors have long been considered to be small and low cost, but their performances are also known to suffer from output instability over time and relatively short operating lives when compared to other non-electrochemical gas sensors, particularly the NDIR types. Over a decade ago, Wong disclosed in U.S. Pat. No. 5,444,249 (Aug. 22, 1995) a miniaturized single beam NDIR gas sensor manufactured using semiconductor micro-machining techniques from a semiconductor material. Since the NDIR sensor is fabricated out of a semiconductor material, the source driver and signal processing electronics can be added directly to the sensor using integrated circuit (IC) fabrication techniques.

Over the past years, the advent of micro electro-mechanical system (MEMS) sensors of all types has driven the available sensor sizes drastically downwards. MEMS devices can comprise one or more mechanical elements such as sensors and actuators formed on a substrate, and silicon substrate, through micro-fabrication technology. Such MEMS devices in a state before packaging can also be referred to as a "MEMS die". MEMS dies are normally placed in a package to protect the MEMS dies and simplify electrical connection to larger electronic devices. Such MEMS packages are typically designed to be attached to a printed circuit board (PCB) or similar interface for larger devices. A MEMS package can include a case defining a cavity to contain a MEMS die, bond pads for electrical connection to the MEMS die, leads for electrical connection to a larger device, and interconnects for electrical connection between the bond pads and the leads. A MEMS die is attached to a mounting surface of the MEMS package, and can be electrically connected to the bond pads. Other devices such as application specific integrated circuit (ASIC) dies can be similarly packaged for protection and to simplify electrical connection to larger electronic devices. Such ASIC dies can be independently packaged or packaged together with MEMS devices. Vertical mounting of MEMS dies has been addressed by Xue et al. in U.S. Pat. No. 8,836,132 B2 (September 2014) and U.S. Pat. No. 8,624,380 B2 (January 2014). In the majority of applications, the MEMS die is parallel to the package mounting plane so that the device is in a horizontal orientation. In other applications, the MEMS die is perpendicular to the package mounting plane, so that the device is held in a vertical orientation.

The requirements for stable infrared sources and detectors along with long path length chambers in order to detect very low concentration of gases are still complications for the MEMS technology to overcome in the future. However, such a promising sensor technology with its own limitations has yet to penetrate into the domain of NDIR gas sensors. From the above discussion it is apparent that the NDIR gas sensors technology can be further improved for miniaturization in concomitant with lower unit cost.

In the field of MEMS, a microheater is a continuous line made of conductive material, which heats up in response to an input current due to Joule's heating. The microheater are popularly used as either microplates for providing localized heating or as infrared source dictated by Planck's radiation law. The heater line is housed on a membrane for mechanical stability and is secured to the substrate through supporting arms. In order to improve the efficiency, miniaturization and improved performance of the microheater, numerous tradeoffs are designed based on the application. Usually, the heater lines are wound in meander shape to achieve improved footprint with high resistance. Furthermore, in order to reduce the heat loss through conduction by the supporting arms, the geometry of these structures are optimized with the desired mechanical strength needed to hold the heater in place. Finally, the heater is packaged in vacuum to reduce the heat loss due to air convection.

A thermopile is a device that converts thermal energy into electrical energy. It is composed of several thermocouples (one P-type beam and one N-type beam) connected together. The device has a hot junction (the absorber) and a cold junction (the substrate) at two ends of the thermocouples. Thermopiles do not respond to absolute temperature, but generate an output voltage proportional to a local temperature difference, thus, maintaining a high temperature difference would increase the output of the device. The phenomena through which one material can convert thermal energy into electrical energy is called thermoelectric effect. The Seebeck coefficient of a material is a measure of the magnitude of an induced thermoelectric voltage in response to a temperature difference across that material. There are generally two ways to increase the output device, using materials with high Seebeck coefficient and maintain a high temperature difference. In a thermopile, the absorber is used to absorb the incident signal (light), and create a temperature difference between two ends of the thermocouple. The design principle of any thermopile can be summarized as 1), a high efficient absorber which converts all incident light to heat. 2), eliminate most or all heat loss between the absorber and Si substrate, which includes conduction, convention and radiation.

Ideally, the only thermal path would be the thermocouples themselves.

Embodiments of the present invention seek to address at least one of the above problems.

SUMMARY

In accordance with a first aspect of the present invention, there is provided a gas sensor comprising a first micro electro-mechanical system (MEMS) die comprising a light source; a second MEMS die comprising a light detector; a sample chamber disposes in an optical path between the light source and the light detector; and a holder substrate; wherein the first and second MEMS dies are disposed on the holder substrate in a vertical orientation relative to the holder substrate, and with the sample chamber disposed laterally there between.

In accordance with a second aspect of the present invention, there is provided a method of manufacturing a gas sensor comprising the steps of providing a first micro electro-mechanical system (MEMS) die comprising a light source; providing a second MEMS die comprising a light detector; providing a sample chamber disposes in an optical path between the light source and the light detector; and providing a holder substrate; wherein the first and second MEMS dies are disposed on the holder substrate in a vertical orientation relative to the holder substrate, and with the sample chamber disposed laterally there between.

In accordance with a third aspect of the present invention, there is provided a method for fabricating a micro electro-mechanical system (MEMS) die for a heater or thermopile, the method comprising providing a support structure; providing one or more metamaterial elements on the support structure; providing the support structure with the one or more metamaterial elements suspended across a cavity; and providing a wafer level thin film encapsulation for vacuum packaging of the MEMS die.

In accordance with a fourth aspect of the present invention, there is provided a micro electro-mechanical system (MEMS) die for a heater or thermopile, the MEMS die comprising a support structure; one or more metamaterial elements on the support structure; the support structure with the one or more metamaterial elements across a cavity; and a wafer level thin film encapsulation for vacuum packaging of the MEMS die.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Figure 1:
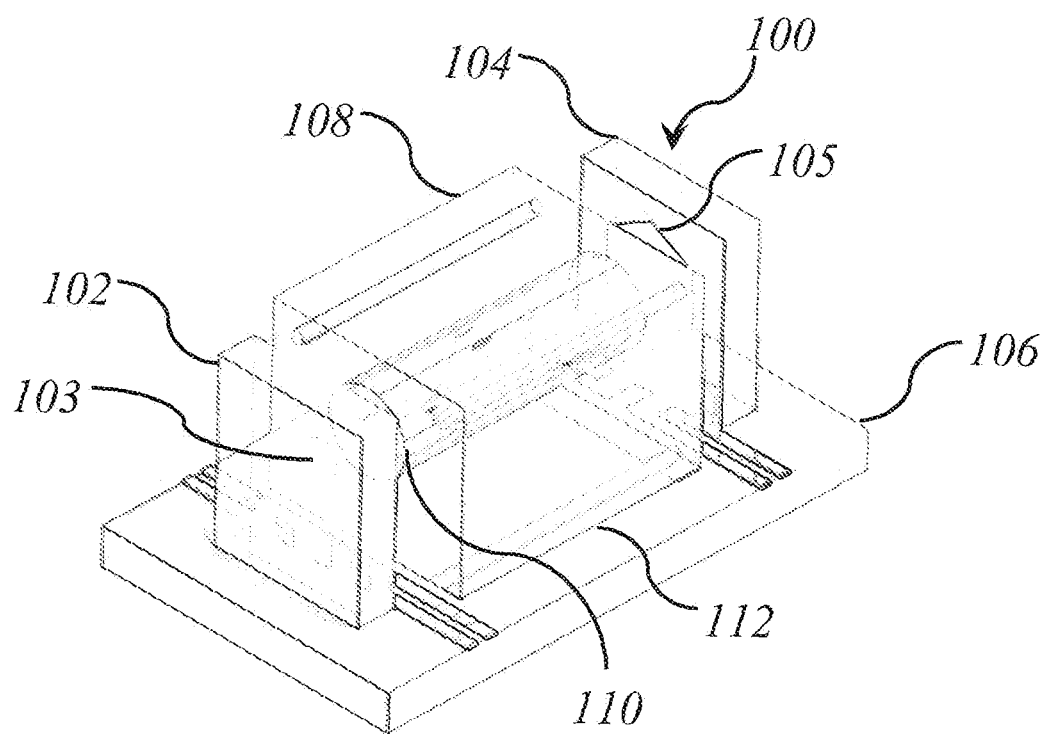
FIG. 1 shows a lien drawing of a single-beam NDIR diffusion gas sensor according to an example embodiment.

Embodiments of the present Invention described herein provide a low-cost and low-power integrated single-beam NDIR diffusion gas sensor for fast detection of a predetermined gas (e.g., $CO_2$). The gas sensor according to example embodiments is generally composed by: a single (or array) MEMS infrared heater source with metamaterial emitter to enable narrow bandpass emission, a single (or array) MEMS infrared thermopile detector with metamaterial absorber to enable narrow bandpass absorption, a silicon holder IC, a MEMS tube waveguide diffusion sample chamber with inner reflective surface and apertures, and a silicon ASIC designed on the same silicon holder IC, which contains circuitry to drive the infrared source with eventually feedback loop to calibrate its temperature, an analog interface to read-out the sensor output, and digital signal processing to determine the concentration of the gas and to compensate the environmental variations, i.e. sample chamber temperature, pressure, and eventually RH. All the components are realized through a CMOS compatible process.

As will be appreciated by a person skilled in the art, "metamaterial" is an artificial material that does not exist in nature but can be engineered to manipulate electromagnetic (EM) wave propagation or achieve the unique features of EM wave which only can be realized on these periodic array of designed unit cell. As for gas sensing, metamaterial can be designed to allow a particular wavelength to propagate for selective reading while eliminating the need for bulk component, e.g., optical filter.

In case multiple components are used in example embodiments, i.e. an array of MEMS infrared heaters and an array of MEMS thermopiles, the radiation through the sample gas can be increased and the radiation detected by the thermopiles maximized. The single components of the array can be connected both in parallel and in series depending on the design chosen.

In some example embodiments, the MEMS die are vertically assembled on the trenches of the holder IC which mechanically supports and electrically connects the die. The ASIC in some example embodiments is designed on the same holder IC containing the driver, analog interface, and digital processing circuitry. The MEMS metamaterial emitter and absorber preferably allow the MEMS infrared microheater source to emit radiation and the MEMS thermopile detector to receive radiation of a wavelength that is strongly absorbed by the gas whose concentration is to be determined. In some example embodiments, the MEMS tube waveguide diffusion chamber is used to transmit the radiation from the infrared source to the thermopile through the sample gas via multiple reflections on the inner surface, while acting as the gas sample chamber. The apertures can allow the gas to enter and exit spontaneously under environmental pressure. In some example embodiments, the thermopile converts the changes of the gas absorption properties into a read-out voltage which is then sampled and processed by the electronics to determine the concentration of the gas and to compensate the environmental variations.

The vacuum level thin film encapsulations according to some example embodiments thermally isolate the source and detector from the sample gas, thus preventing the sample gas or the air from cooling these elements. In addition, the thermal isolation preferably reduces the thermal response time of source and detector, thus allowing a very fast gas detection and hence low energy consumption per measurement, while increasing the yield. Because the inner surface of the MEMS tube waveguide is reflective in some example embodiments, radiation is transmitted from the source to the detector through the sample gas without the need for expensive optics. In addition, because this gas sensor in some example embodiments uses a diffusion gas sample chamber, no pump is required to push or pull the sample gas into the sample chamber.

Figure 2:
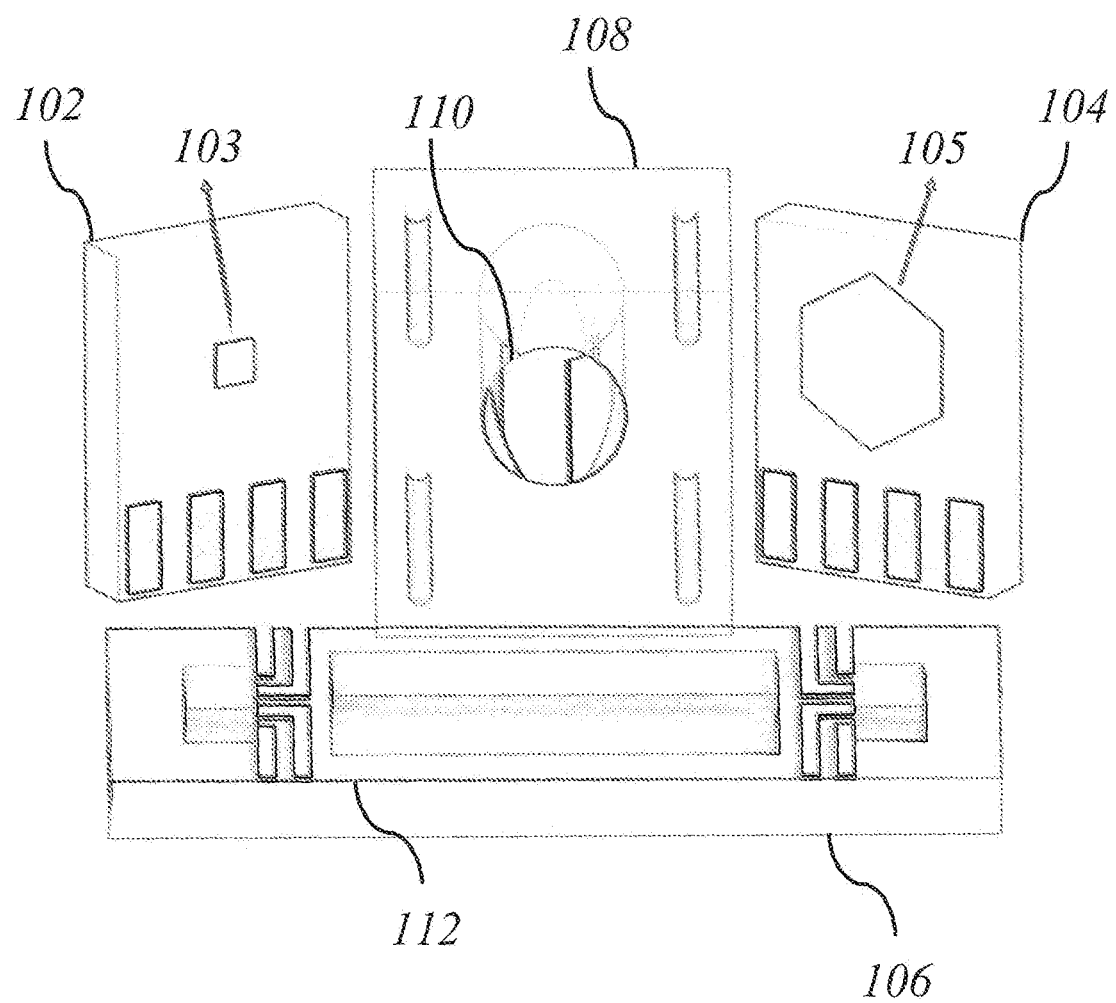
FIG. 2 shows a line drawing of the separated parts of the sensor of FIG. 1.
Figure 3:
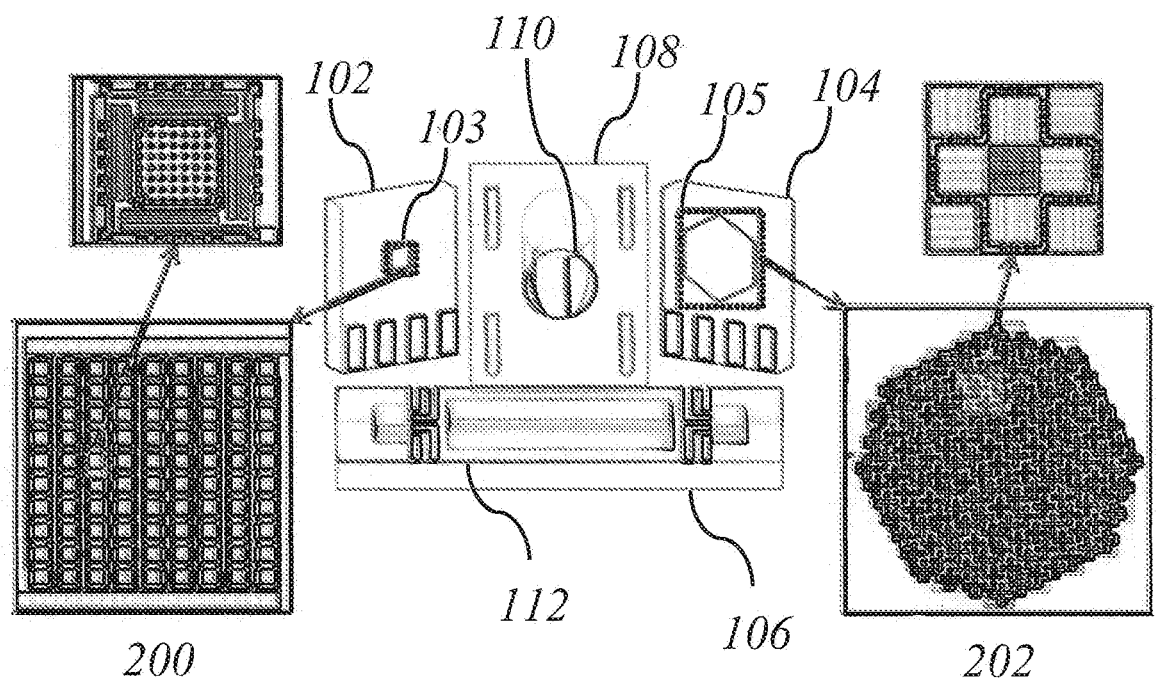
FIG. 3 shows a line drawing of the separated parts of the sensor of FIG. 1 modified according to another example embodiment.

The novel low-cost and low-power integrated single-beam NDIR diffusion gas sensor 100 for fast detection of a predetermined gas according to an example embodiment of the present Invention is shown in FIG. 1. The sensor 100 includes a MEMS die 102 comprising a single (or array, compare FIG. 3) MEMS source 103 with metamaterial emitter and vacuum level thin film encapsulation (not resolved), a MEMS die 104 comprising a single (or array, compare FIG. 3) MEMS detector 105 with metamaterial absorber and vacuum level thin film encapsulation (not resolved), a silicon holder IC 106, a MEMS die 108 comprising a MEMS tube waveguide diffusion sample chamber 110 with inner reflective surface and apertures in the form of the open ends of the chamber 110, and a silicon ASIC 112 designed on the same holder IC 106 which comprises a source driver, analog interface, and digital processing circuitry (not resolved). The separated parts of the sensor 100 according to the example embodiment of FIG. 1 are shown in FIG. 2, with the same reference numerals as in FIG. 1 used for the same parts. In addition, FIG. 3 shows the separated parts of a modified embodiment, with corresponding parts having the same numeral as in FIGS. 1 and 2 but with a "b" added, including micro heaters and thermopiles arrays 200, 202, respectively, providing a sensor including multiple source and detector MEMS components.

The holder IC 106 can be fabricated from a semiconductor material using existing techniques understood in the art, whereas the MEMS die 102, 104 and 108 can be vertically mounted on the holder IC 106 using a standard die-attaching process. As will be appreciated by a person skilled in the art, die-attaching process is the process of attaching the MEMS die either to a package or to some substrate. Some examples of die-attaching process include eutectic bonding, epoxy bonding, and solder attach. Specific advantages of the vertically mounted MEMS dies include miniaturization capability and Line-of-Sight (LoS) radiation between source and detector. Other advantages include easiness of integration and assembly. Vertical mounting represents a cornerstone technology for System-on-Chip (SoC) and System-in-Package (SiP) solutions with high-aspect ratio for mass production. Any semiconductor material may be used for the holder IC 106 including silicon (Si) and gallium arsenide (GaAs), however Si is presently considered the preferred semiconductor material. Other semiconductor materials that may be used include binary, ternary, and quaternary II-VI and III-V semiconductor materials.

The vacuum encapsulations thermally isolate the source and the detector from the gas sample in some example embodiments so that the gas sample (or air) does not cool the detector or source, which would result in an incorrect reading. The thickness of the encapsulation is selected to achieve thermal isolation while at the same time permitting to be optically transparent.

The source 103 produces broadband radiation of all wavelengths. The sample chamber 110 contains the gas sample to be examined for the concentration of a particular gas. Radiation entering the sample chamber 110 passes through the gas sample until it is detected by the detector 105. The source 103 can be realized in some embodiments by a thin film resistive heating element, i.e. a heater, placed on a cantilever so as to thermally isolate it from the substrate. The resistive element can be made of polycrystalline silicon (Polysilicon) or other suitable metals such as platinum (Pt). Preferably, the heater materials are carefully selected to ensure high temperature performance. In addition, thermal isolation of the heating element is preferred to keep small the thermal response time of the source 103, and so that the entire substrate is not heated. In addition, a cantilever preferably prevents heat produced by heating element from draining to substrate too quickly.

The metamaterial emitter and absorber in some embodiments permit selective narrowband emission for the source 103 and selective narrowband absorption for the detector 105. The metamaterial can be made of molybdenum (Mo) or other suitable metals. Preferably, the metamaterial materials are carefully selected to ensure high temperature performance. The specific wavelength of the metamaterial depends on the absorption spectrum of the targeted gas, and it can be easily changed to other wavelength of interest by modifying the metamaterial pattern. The specific wavelength of the metamaterial can be configured to detect the concentration and/or presence of various gases including, but not limited, to $CO_2$, carbon monoxide (CO), oxygen ($O_2$), hydrogen sulfide ($H_2S$), nitrogen dioxide ($NO_2$), sulfur dioxide ($SO_2$), etc. For example, a metamaterial with a center wavelength of 4.26 µm and a full width at half maximum (FWHM) of about 0.1-0.2 µm is appropriate for $CO_2$ detection. Since the source 103 and detector 105 employ a metamaterial layer, the sensor 100 advantageously does not require any additional stand-alone and expensive bandpass filter (filter-free design).

The detector 105 in example embodiments may be any device that creates variable electrical responses to corresponding variations in the strength of radiation reaching it from the source. Any detectors may be used when measuring infrared radiation: thermopile, thermocouple, pyroelectric, and bolometer. However, a thermopile detector may be favored for the detection of infrared radiation. A thermopile responds to temperature changes caused by the radiation incident upon it, and thus converts the radiation into electrical energy.

The sample chamber 110 is a diffusion type gas sample chamber in some embodiments. Hence, no pumps are required to push or pull the gas sample into the sample chamber 110. In some embodiments the two ends of the waveguide forming the chamber 110 act as apertures which let the gas diffuse into and out of sample chamber 110. The apertures can have a wide range of shapes and sizes. For instance, an aperture size of 20 µm or more allows diffusion of gas through it rapidly enough so that a response to a change in composition of the surrounding air can be register within about 10 s after a composition change occurs. Moreover, it is desirable to prevent particles of dust and smoke from entering sample chamber 110. Hence, apertures can be covered with a gas semi permeable membrane in some embodiments, which preferably keeps out particles of a size greater than about 0.1 µm. The gas semi-permeable membrane may be a dielectric layer that can be deposited by evaporation or sputtering. Silicon oxide, silicon nitride, Teflon, and Kapton are dielectrics suitable for this purpose, preferably the dielectric layer is silicon oxide or silicon nitride. For ease of assembly, it is preferable that the sample chamber 110 has a square or rectangular cross-section, however, other shapes can be used such as a circular or triangular waveguide in different embodiments.

The inner surface of the circular waveguide tube forming the chamber 110 is metallized in some embodiments in order to improve the efficiency of the sensor. A variety of different metallization can be used to increase the reflectivity of the inner surface, including aluminum (Al), gold (Au), chromium (Cr), nickel (Ni), and Pt. Each of these metals can be deposited on the inner surface of the waveguide using vapor deposition or electroplating, or directly by attaching a thin metal film.

The source driver of the ASIC 112 energizes the source 103 through a duty-cycled electric current in some embodiments. The driver includes circuitry to drive the source 103 and preferably includes a feedback loop to calibrate the source's 103 temperature. After the radiation from source 103 reaches the detector 105, the latter produces an electrical signal that represents the intensity of the radiation falling on it. This signal is inversely proportional to the amount of gas being detected. For example, if $CO_2$ is being detected, the more $CO_2$ there is in the sample chamber 110 the weaker the infrared energy will be striking the detector 105.

The analog interface and digital processing electronics of the ASIC 112 elaborate the electrical signal produced by detector 105 thus providing the concentration of the targeted gas and compensating for environmental variations in some embodiments. Therefore, the signal output of the processing electronics may be applied to a meter or an alarm as is understood in the art. In another embodiment, the analog interface and digital processing electronics of the ASIC 112 can be coupled also with the source 103. The source driver, analog interface, and digital processing electronics are realized within e.g. a silicon ASIC 112 on the same holder IC 106. The signal produced by the detector 105 can be a time-varying response in reaction to a certain gas concentration (or gas mixture) which depends on several factors such as: type of sensor, nature and concentration of the gas, reaction of the gas with the sensor components, and environmental conditions. These elements, together with the intrinsic noise of the detector 105, give unstable responses over time, thus a double beam device generally mitigate these deficits, with the reference beam acting as a reference for detection of the gas species over time. However, this will increase dramatically the cost and size of the sensor 100. Nevertheless, appropriate signal processing algorithms can mitigate the aforementioned deficits with a single beam sensor (filter-free design) 100 by extracting the useful information from the sensor responses and predicting accurately the related gas concentrations. Furthermore, data acquisition from the detector 105 is normally performed by saving the static (steady-state) values of sensor responses and by ignoring the dynamic (transient) values that may bring beneficial information. While the steady-state approach works well for some applications, recent studies suggest that the dynamic responses contain useful information including the thermal behavior of the sensor which depends on sensor type and components and on gas nature and concentration. The source 103 is normally not operated continuously, but it is rather pulsed at a specific frequency to reduce the usage of the sensor 100 and decrease the overall power consumption (i.e., prolonging its lifetime). In traditional methods, the response time dictated by the time required to reach 90% of the thermal steady state is typically in the order of seconds or even longer. Hence the measured gas concentration is available only after the response time, which implies greater energy consumption per measurement. Transient analysis methods can reduce the latency between a gas concentration raise and its detection, compared to traditional slower methods based on steady-state analysis. Therefore, transient analysis can enable true real-time sensing, and hence quick reaction to time-varying (and potentially hazardous) environmental conditions, before excessive gas concentration occurs. In addition, transient analysis enables low energy consumption per measurement and scalable energy-accuracy tradeoff by targeting a desired accuracy achieved by assigning an appropriate measurement time. Several fast circuit and hardware solutions of the ASIC 112 have been proposed to reduce the response time, although at the price of higher sensor cost and/or larger size. On the other hand, the analysis of the transient sensor response through signal processing algorithms of the ASIC 112 represents a better and cost-effective option to enable real-time sensing. The signal processing unit of the ASIC 112 processes the transient sampled sensor response through real-time signal processing algorithms in order to derive the gas concentration. A variety of features can be added to the signal processing unit of the ASIC 112 to improve the robustness of the algorithm against fluctuations in the environmental including ambient temperature, pressure, RH, radiation source temperature, and many others. A wide variety of signal processing algorithms of the ASIC 112 can be used to predict the gas concentration from the transient sampled sensor response. A few non-exhaustive examples include ordinary least-squares regression (OLS), multiple linear regression (MLR), principal component regression (PCR), partial least-squares regression (PLS), Ridge regression (RR), Lasso regression (Lasso), multivariate adaptive regression splines (MARS), stepwise regression (SR), nonlinear regression, and many others. In addition, classification techniques can be used such as linear discriminant analysis (LDA), logistic regression (LR), classification and regression trees (CART), Gaussian mixture models (GMMs), k-nearest neighbors (k-NNs) classification, artificial neural networks (ANNs), support vector machines (SVMs), partial least-squares-discriminant analysis (PLS-DA), multilayer perceptron classifiers (MLPs), radial basis functions (RBFs), etc. Other possible examples include feature extraction techniques such as genetic algorithms (GAs), feature subset selection (FSS), sequential forward selection (SFS), sequential backward selection (SBS), best-subset regression, etc.

Because of the diffusion type gas sample chamber 110 in some embodiments, if the environmental temperature falls sufficiently, condensation of air (water vapor) or other gases can occur in the form of small droplets deposited on the internal walls of gas sample chamber. This can interfere with the internal reflectivity that is desired for operation of the waveguide forming the chamber 110, thus leading to erroneous results. A solution according to some embodiments is to add a thin film resistive type heater and resistance temperature detectors (RTDs) to the sidewalls of optical waveguide forming the chamber 110. The heaters and RTDs can be connected to a temperature control circuit to keep the sample chamber 110 at an established temperature. As with the source driver, analog interface, and digital processing electronics, the temperature control circuit can be integrated within a silicon ASIC 112 on the same holder IC in some embodiments.

In order to enhance the performance of the NDIR gas sensor according to some embodiments of the present Invention, other semiconductor IC/MEMS sensors may be added wherever desirable such as temperature, pressure, and RH sensors. For instance, a temperature sensor can be realized through a MEMS resistive heater which is placed close to the main source heater in some embodiments. Since both temperature sensor and source are subjected to the same temperature, the temperature sensor can be used to detect the heater temperature, and then pass this feature to the feedback loop circuitry which will adjust the heater current accordingly to keep the heater temperature (and power) constant. As another example, a micro-flow sensor may be added to detect the flow rate of the sample gas over the sample chamber in some embodiments. The output from these devices can be connected to the electronics within the silicon ASIC in some embodiments.

Some embodiments of the present Invention can also be used to determine simultaneously multiple gas concentration by using metamaterials with different emission and absorption wavelength, and by processing the detector output signal by classification and/or regression learning techniques. These methods can preferably recognize multiple gases even with a single-beam device with a single detector.

Embodiments of the present Invention can be linked to a WSN that connects to a plurality of others gas sensors.

In one embodiments a gas sensor is provided, comprises a first micro electro-mechanical system (MEMS) die comprising a light source; a second MEMS die comprising a light detector; a sample chamber disposes in an optical path between the light source and the light detector; and a holder substrate; wherein the first and second MEMS dies are disposed on the holder substrate in a vertical orientation relative to the holder substrate, and with the sample chamber disposed laterally there between.

The light detector may comprise one or more conversion elements for converting a temperature change into an electrical signal and one or more first metamaterial elements thermally coupled to respective ones of the conversion elements, the first metamaterial elements configured for selective absorption at one or more wavelengths emitted by the light source and means for converting changes in the absorption at the one or more wavelengths into a variable electrical response.

The gas sensor may further comprise vacuum level thin film encapsulations for the first and second dies, respectively, for thermal isolation of the light source and the light detector from a gas sample.

The light source may comprise one or more heater elements and one or more second metamaterial elements thermally coupled to respective ones of the heater elements, the second metamaterial elements configured for emission at the one or more wavelengths.

The gas sensor may further comprise a processing circuit with, at least, a source driver for driving the light source and an analogue interface coupled to the light detector. The processing circuit may be integrated on the holder substrate.

The sample chamber may comprise a waveguide diffusion chamber. Opposing open ends of the waveguide diffusion chamber function as diffusion apertures.

Figure 10:
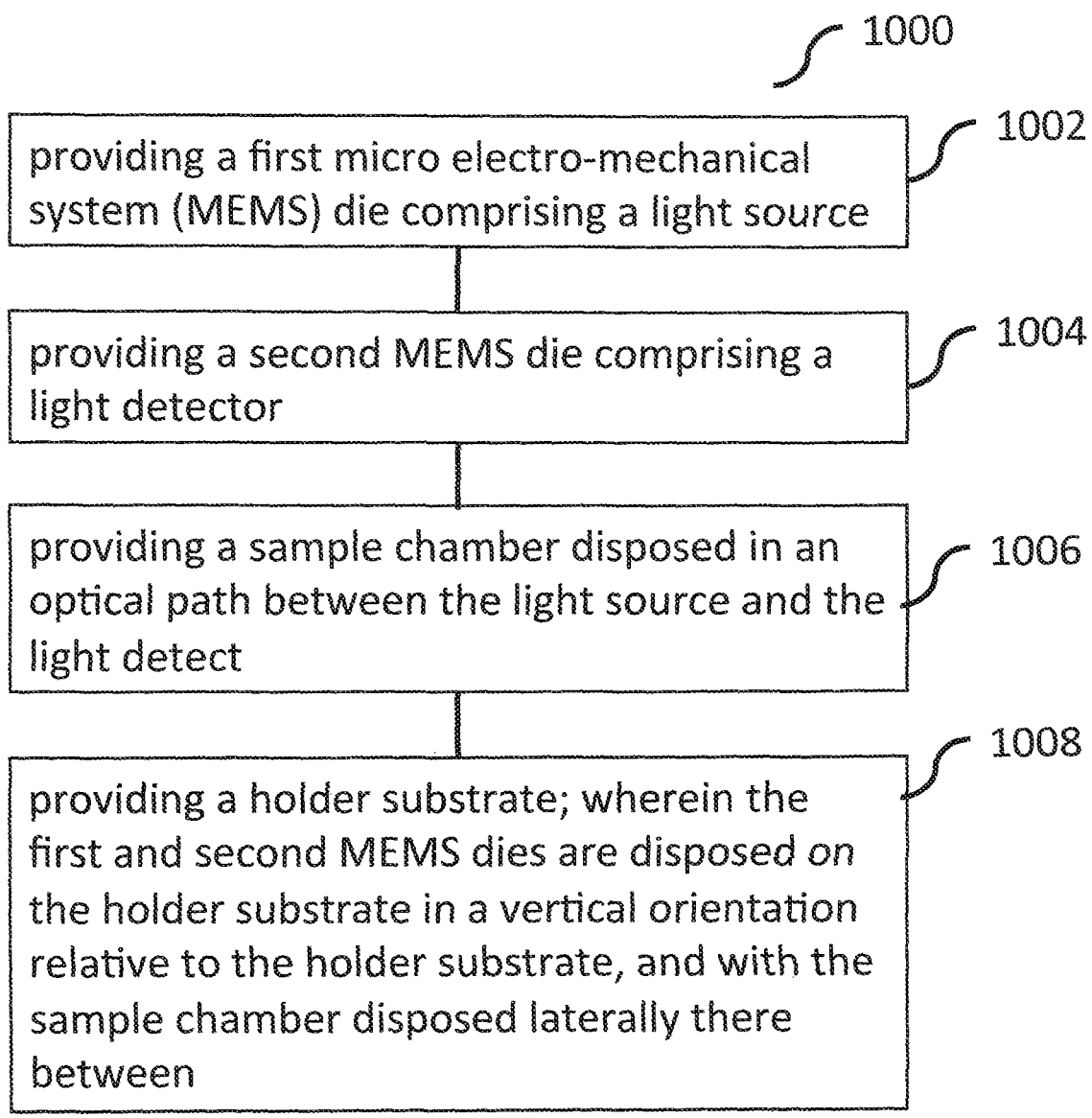
FIG. 10 shows a flow chart illustrating a method of manufacturing a gas sensor according to one embodiment.

FIG. 10 shows a flow chart 1000 illustrating a method of manufacturing a gas sensor according to one embodiment. At step 1002, a first micro electro-mechanical system (MEMS) die comprising a light source is provided. At step 1004, a second MEMS die comprising a light detector is provided. At step 1006, a sample chamber disposed in an optical path between the light source and the light detector is provided. At step 1008, a holder substrate is provided, wherein the first and second MEMS dies are disposed on the holder substrate in a vertical orientation relative to the holder substrate, and with the sample chamber disposed laterally there between.

Providing the light detector may comprise providing one or more conversion elements for converting a temperature change into an electrical signal and thermally coupling one or more first metamaterial elements to respective ones of the conversion elements, the first metamaterial elements configured for selective absorption at one or more wavelengths emitted by the light source and means for converting changes in the absorption at the one or more wavelengths into a variable electrical response.

The method may further comprise providing vacuum level thin film encapsulations for the first and second dies, respectively, for thermal isolation of the light source and the light detector from a gas sample.

Providing the light source may comprise providing one or more heater elements and thermally coupling one or more second metamaterial elements to respective ones of the heater elements, the second metamaterial elements configured for emission at the one or more wavelengths.

The method may further comprise providing a processing circuit with, at least, a source driver for driving the light source and an analogue interface coupled to the light detector. The method may comprise integrating the processing circuit on the holder substrate.

The sample chamber may comprise a waveguide diffusion chamber. Opposing open ends of the waveguide diffusion chamber function as diffusion apertures.

It is noted that while the embodiments described above use metamaterial elements in the light source and the light detector, the present invention may also be implemented with traditional filter(s) in the light source and/or light detector in different embodiments.

Embodiments of the present invention can have one or more of the following features and associated advantages:

Integrated single-beam NDIR diffusion gas sensor with MEMS die that are vertically mounted and electrically connected on a silicon holder IC: Reduces the fabrication cost and allow extreme miniaturization with lower unit cost within a CMOS compatible process.

Vacuum level thin film encapsulated MEMS parts: fast thermal response thus quick detection, and hence low energy consumption per measurement, within a single chamber: Reduces the cost of MEMS parts, since no further packaging needed, while increasing the yield.

Metamaterial MEMS emitter and absorber: Allow selective emission and absorption for specific wavelength (easy to change) without the need for an additional stand-alone bandpass filter (filter-free design).

Silicon ASIC designed on the silicon holder IC: Contain the source driver, analog interface, and digital processing circuitry to calibrate and compensate the sensor and to determine the gas concentration.

Waveguide diffusion MEMS gas sample chamber: Simplifies the system in a single chamber, reducing the fabrication cost without the need of expensive optics.

Energy-accuracy scalable performance: The energy per measurement can be flexibly traded off with the gas sensor accuracy (i.e., prediction error) by simply increasing the measurement time.

Fast transient low-energy gas detection system: Transient (dynamic) acquisition with accurate reading while avoiding the traditionally long time required by thermal steady-state (static) measurements.

Low energy consumption per measurement: Quick detection decreases the heating time of the radiation source, thus reducing the energy consumption in each measurement.

Extended gas sensor lifetime: The fast acquisition process reduces the exposure time of the sensor components to the gas, thus mitigating reliability issues and prolonging the sensor lifetime Dynamic processing of sensor response: Signal processing algorithms enhance the accuracy by mitigating the effect of the sensor noise during the measurement.

Robustness against environmental variations and radiation source drift/aging: Signal processing techniques allow sensor self-calibration and suppression of ambient fluctuations and source drift/aging.

The main commercial applications of embodiments of the present Invention can include:

Internet of Thing (IoT) applications

Wearable and Smartphone systems

Heating, ventilation and air conditioning (HVAC) systems

Demand-controlled ventilation (DCV) systems

Indoor air quality (IAQ) applications

Non-dispersive infrared (NDIR) measurement of gas concentration

Distributed $CO_2$ sensing

Green buildings

Infrared spectroscopy

Gases detection

Hazardous-Gas detection

Material Characterization

Fire & Flame Detection

Radiometers

It is noted that while the embodiments described above with reference to FIGS. 1 to 3 relate to NDIR gas sensors, the present invention can be applied to different type of light-emission and -detection based gas sensors such as optical gas sensors, spectroscopic gas sensors, mid infrared (IR) gas sensors, mid infrared (IR) light-emission diodes (LEDs) and photodiodes. It is also noted that the architecture described for the embodiments with referenced to FIGS. 1-3 can be used with different sources (e.g. resistive heater, thin-film heater) and detectors (e.g. thermopile, pyroelectric, bolometer) types.

In the embodiments described above, a metamaterial layer or layers are advantageously included in a gas sensor architecture to provide selective (i.e. narrow bandpass) emission/absorption for specific wavelengths. This can provide a filter-free gas sensor design, which in turn can reduce complexity and/or costs according.

Figure 4:
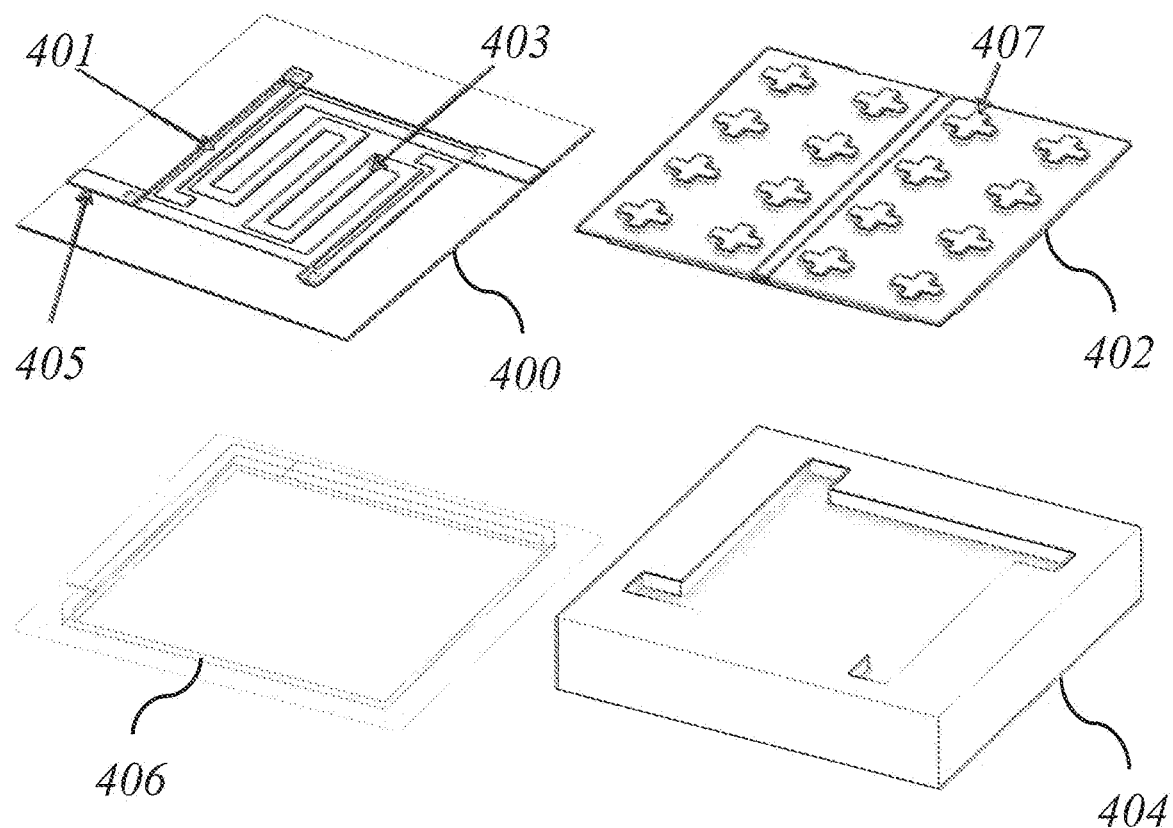
FIG. 4 shows a line drawing of components of a micro-heater device according to an example embodiment.

In another aspect, embodiments of the present Invention can provide a micro-heater device. The micro-heater device according to one embodiment generally includes four parts as shown in FIG. 4: the heater 400 (with supporting arms e.g. 401, PolySi heater wire 403, and metal interconnects e.g. 405), the emitter 402 (with metamaterial pattern 407), the cavity 404, and the encapsulation 406.

The micro-heater devices according to some embodiments are light sources that emit broadband radiation. The wavelengths can extend from visible to the far infrared. The broadband nature of the radiation makes these micro-heater devices/sources useful in spectrophotometry and infrared-signal generation, e.g. for use in the embodiments of the sensor described above with reference to FIGS. 1 to 3. In the micro-heater device according to some embodiments, the electrical current going through the conductive wire heats the emitter, by joule heating. The emitter converts the heat to light. The design principle of the micro-heater device according to some embodiments can be summarized as 1) A high efficient emitter which converts heat to light. 2) Eliminate most or all heat loss between the emitter and Si substrate, which includes conduction, convention and radiation. The only thermal path would preferably be the supporting arms. 3) The supporting arms should preferably have a low thermal conductivity.

The heater 400: Polycrystalline silicon (Polysilicon) can be used for the heater 400. Silicon has a few advantages including much lower thermal conductivity compares to metal. Silicon reduces the energy loss through the supporting arms. In traditional fabrication process, a dielectric layer is right beneath the Polysilicon layer to provide the insulation. The dielectric layer is an additional heat loss path other than the Polysilicon layer. It also induces residual stress to the devices but do not have any other benefit other than electrical insulation. In the process flow according to some embodiments described below, this dielectric layer is preferably eliminated while still maintaining a good insulation for the device. Polysilicon also has a higher resistivity than metal, which preferably makes sure most of the joule heating happens on the heating wire other than the metal interconnection outside of the device in some embodiments.

The emitter 402: A metamaterial pattern 407 is designed for the emitter 402 in some embodiments. The metamaterial pattern 407 can be engineered to emit light with specific wavelength only, and have a 100% emission rate in the peak wavelength. In this way, the emitter 402 can preferably only emit the interested wavelength, which is a great advantage for gas sensing applications.

The cavity 404: During the fabrication of the microheater device 500 in some embodiments, the emitter 402 and the heater 400 need to be released. By suspending the emitter 402 and supporting arms e.g. 401 of the heater 400, the dominated heat loss mechanism (thermal conduction through solid) is preferably removed. Using a conventional process understood in the art, the release step can be done by an isotropic etch controlled by time. After the etching, the emitter 402 and the supporting arms e.g. 401 of the heater 400 are fully released, but the side effect is the supporting arms e.g. 401 may be over released. In full wafer fabrication, increase the release time could preferably ensure all devices on the wafer are released. The micro-heater device 500 can be packed with higher density since over release would not have influence to the micro-heater device 500 according to some embodiments, since the physical connection between the supporting arms e.g. 401 (and thus the heater 400) and the substrate outside the cavity is formed by separate connection structures, as will be described in more detail below with reference to FIG. 7. Briefly, due to the existence of non-etchable layers which are shaped into the other functional parts and these non-etchable layers being connected to substrate, only the sacrificial material inside the cavity is removable in the conventional isotropic etching. Thus, increasing the release time could ensure all devices on the cavity are fully suspended while these devices advantageously will not be detached from wafer after releasing, according to some example embodiments.

The encapsulation 406: Because of the heat on the emitter 402 lost via the conduction and convention of air, the performance of the devices could enhance by packaging the devices into vacuum environment. The conventional vacuum packaging method understood in the art uses wafer to wafer bonding. It is an expensive method and the yield is not ideal. In some embodiment, a wafer level thin film encapsulation method preferably replaces the wafer to wafer bonding method. By encapsulating each device individually with a CMOS compatible process in some embodiments, the cost of the device can be reduced.

Figure 5:
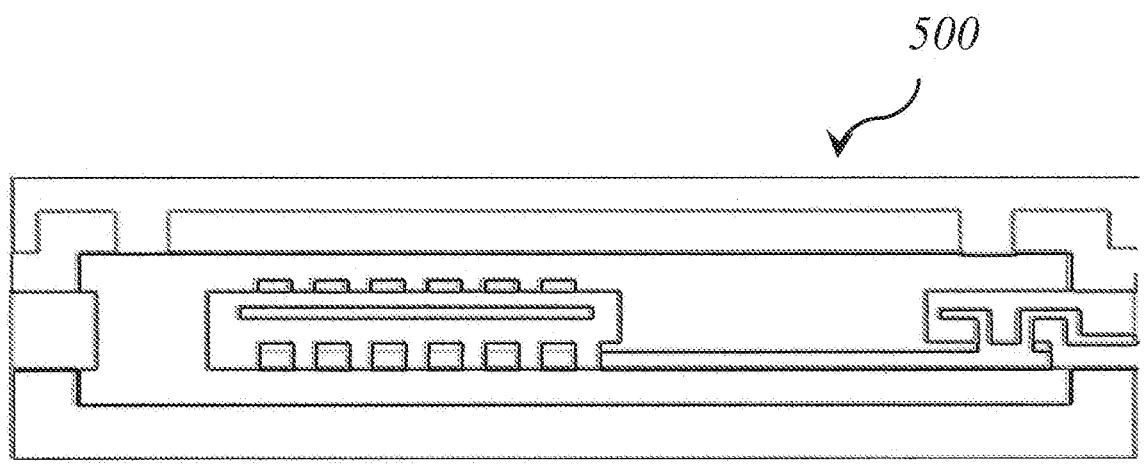
FIG. 5 shows a line drawing of the cross-section of a micro-heater device according to an example embodiment.

The cross-section of a micro-heater device 500 according to an example embodiment is shown in FIG. 5. As will be appreciated by a person skilled in the art, emission is the reverse progress of absorption according to Kirchhoff's law so a metamaterial emitter can have the exact same architecture as metamaterial absorber that consists of bottom metal, middle dielectric and top metal layer. In terms of a metamaterial absorber, the bottom metal layer blocks light from transmission. The top metamaterial and middle dielectric layers can be engineered to achieve specific values of permittivity and permeability to achieve impedance matching with the free space to obtain the absorption resonance. The middle dielectric layer is also used to contain and confine the resonance and reduce energy loss. The structures are designed for perfect absorption, i.e., perfect emission at a specific wavelength, preferably enabling high signal to noise ratio of the system at low power consumption.

Figure 6:
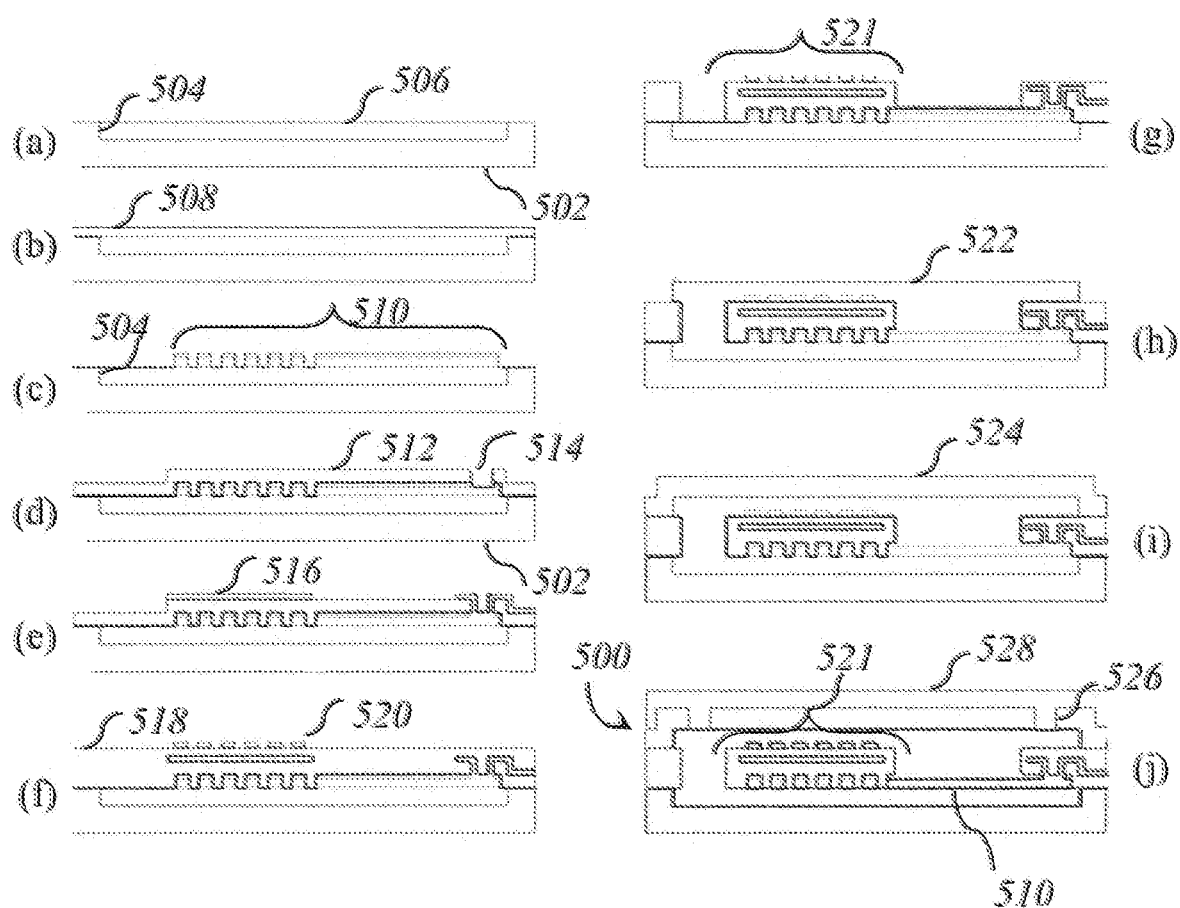
FIG. 6a) to j) shows respective line drawings illustrating the process flow of fabricating the microheater device of FIG. 5.

The process flow of fabricating the microheater device 500 is described below with reference to FIG. 6. The process begins with a Si wafer 502. A cavity 504 is first etched on the silicon (Si) wafer 502 for 2 μm. A silicon dioxide ($SiO_2$) layer 506 of thickness more than 2 μm is deposited on the whole wafer 502 and then the $SiO_2$ layer 506 is planarized by chemical mechanical polishing (CMP), as shown in FIG. 6a). A Polysilicon layer 508 is deposited and then doped as N-type or P-type Polysilicon, as show in FIG. 6b). The Polysilicon layer 508 is etched with $SiO_2$ hard mask to form the supporting arms and heater wire, together indicated with numeral 510. The Polysilicon arms are only located within the $SiO_2$ cavity 504 without any physical connection with the Si substrate 502, as shown in FIG. 6c). Aluminum oxide ($Al_2O_3$) 512 is deposited, this layer 512 serves as the insulation layer for the metal interconnection later. The $Al_2O_3$ layer 512 is also the physical connection between the supporting arms 510 and Si substrate 502, as well as the arms 510 and metamaterial emitter. Vias 514 are opened on the $Al_2O_3$ layer 512 to allow electrical interconnection to form with the Polysilicon 508, as shown in FIG. 6d). Molybdenum Metal (Mo) 516 is deposited and etched. This metal layer 516 works as the interconnection between Polysilicon arms 510 and also is the bottom layer of the metamaterial structure, see FIG. 6e). Another layer of dielectric 518 and another layer of metal 520 is deposited and the metal layer 520 is etched to form the metamaterial pattern for the top layer of the metamaterial emitter structure, with a portion of the dielectric layer 518 forming the middle dielectric of the metamaterial absorber, as shown in FIG. 6f). The $Al_2O_3$ is selectively removed above the Polysilicon arms 510, and also forms the shape of the emitter 521, as shown in FIG. 6g). A thick layer of $SiO_2$ 522 is deposited and planarized. The $SiO_2$ 522 is etched and the $SiO_2$ 522 is left above the device, as shown in FIG. 6h). Aluminum nitride (AlN) 524 is deposited to seal the device, as shown in FIG. 6i). On the AlN layer 524, release holes 526 are etched. Vapor Hydrofluoric acid release is conducted to suspend the emitter 521 and arms 510. The device is again sealed with another layer of $SiO_2$ 528 as shown in FIG. 6j). Electrical contact pads (not shown) are opened and formed outside the encapsulation.

Figure 7:
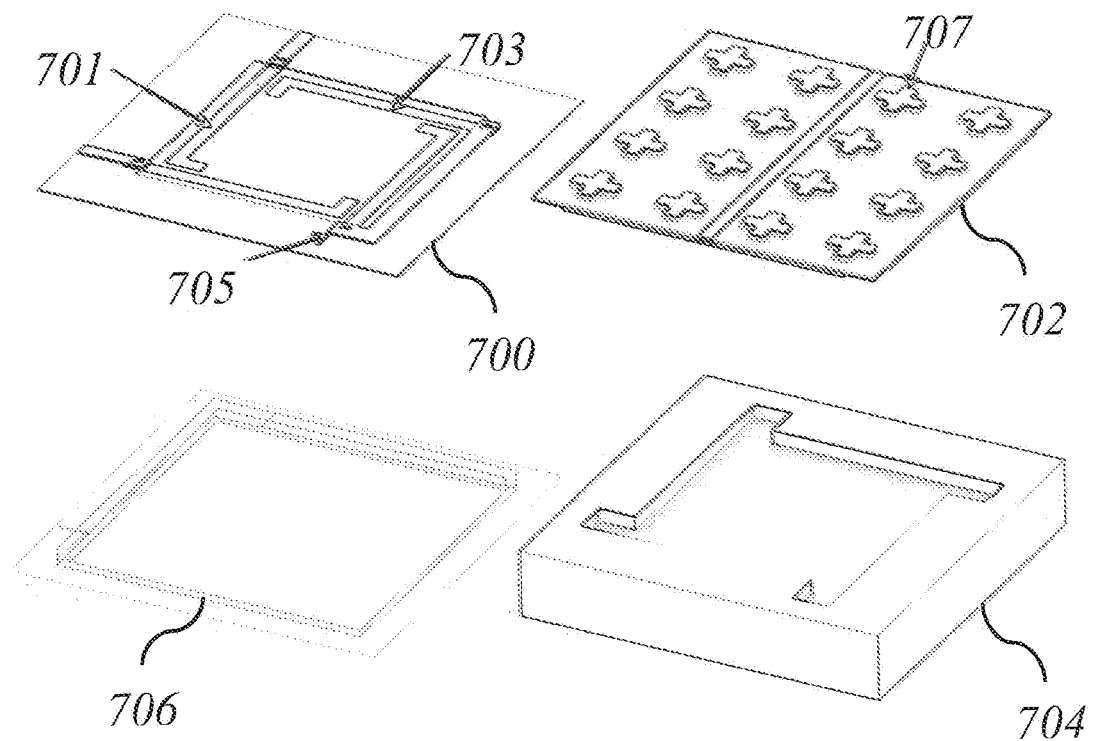
FIG. 7 shows a line drawing of a thermopile device according to an example embodiment.

In another aspect, embodiments of the present Invention can provide a thermopile device. The thermopile device generally includes four parts as shown in FIG. 7: The thermocouples 700 (with P-type PolySi e.g. 701 and N-type PolySi e.g. 703, and metal interconnects e.g. 705, absorber 702 (with metamaterial pattern 707), cavity 704, and the encapsulation 706.

The thermocouples 700: Polysilicon is used for the thermoelectric material in some embodiments as it has a few advantages such as: high Seebeck coefficient, CMOS compatible process, easy to form N-type and P-type material, low residual stress. In traditional fabrication process understood in the art, a dielectric layer is right beneath the Polysilicon layer to provide the insulation. The dielectric layer is an additional heat loss path other than the Polysilicon layer, decreases the temperature difference of the hot junction and cold junction, and induces residual stress to the devices but do not have any other benefit other than insulation. In the process flow according to some embodiments described below, this dielectric layer is preferably eliminated while still maintaining a good insulation for the device.

The absorber 702: A metamaterial absorber is designed for the absorber 702 in some embodiments. The metamaterial can be engineered to absorb light with specific wavelength only, and have a 100% absorption rate in the peak wavelength. In this way, the absorber 702 can preferably only respond to the interested wavelength.

The cavity 704: During the fabrication of the thermopile device in some embodiments, the absorber 702 and the thermocouples 700 need to be released. By suspending the absorber 702 and thermocouples 700, the dominated heat loss mechanism (thermal conduction through solid) is preferably removed. Using a conventional process understood in the art, the release step can be done by an isotropic etch controlled by time. After the etching, the absorber 702 and the thermocouples 700 are fully released, but the side effect is the cold junction of the thermocouples 700 might over release and not closely connected to the substrate. The temperature gradient then is not fully dropped on the thermocouples 700 and the output voltage would decrease. Adding the cavity 704 preferably ensures the cold junction connected to the substrate as design and increases the tolerance of the release time. In full wafer fabrication, increasing the release time could preferably ensure all devices on the wafer are released.

The encapsulation 706: Because of the heat on the absorber 702 lost via the conduction and convention of air, the performance of the devices could enhance by packaging the devices into vacuum environment. The conventional vacuum packaging method understood in the art uses wafer to wafer bonding. It is an expensive method and the yield is not ideal. In some embodiments, a wafer level thin film encapsulation method preferably replaces the wafer to wafer bonding method. By encapsulating each device individually with a CMOS compatible process in some embodiments, the cost of the device can be reduced.

Figure 8:
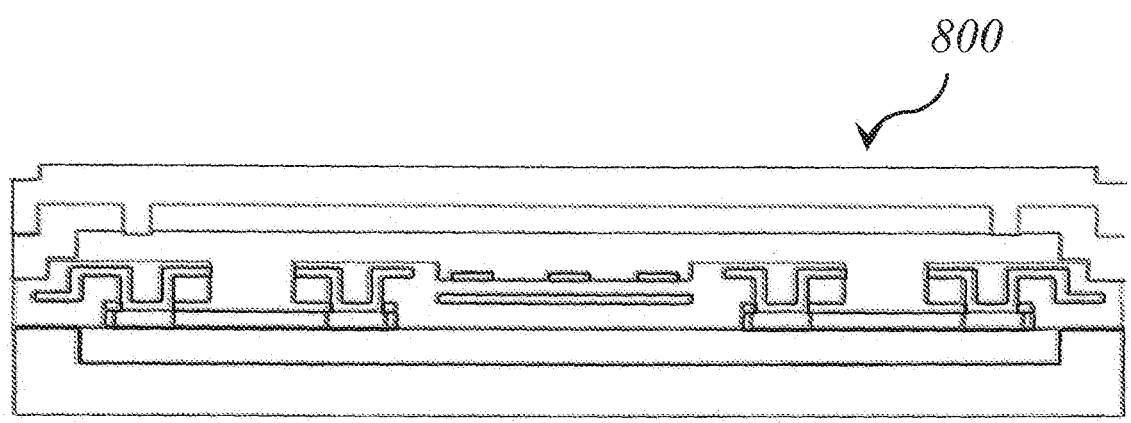
FIG. 8 shows a line drawing of the cross-section of a thermopile device according to an example embodiment.

The cross-section of thermopile device 800 according to an example embodiment is shown in FIG. 8. As will be appreciated by a person skilled in the art, in terms of a metamaterial absorber, the bottom metal layer blocks light from transmission. The top metamaterial and middle dielectric layers can be engineered to achieve specific values of permittivity and permeability to achieve impedance matching with the free space to obtain the absorption resonance. The middle dielectric layer is also used to contain and confine the resonance and reduce energy loss. The structures are designed for perfect absorption, i.e., perfect emission at a specific wavelength, preferably enabling high signal to noise ratio of the system at low power consumption.

Figure 9:
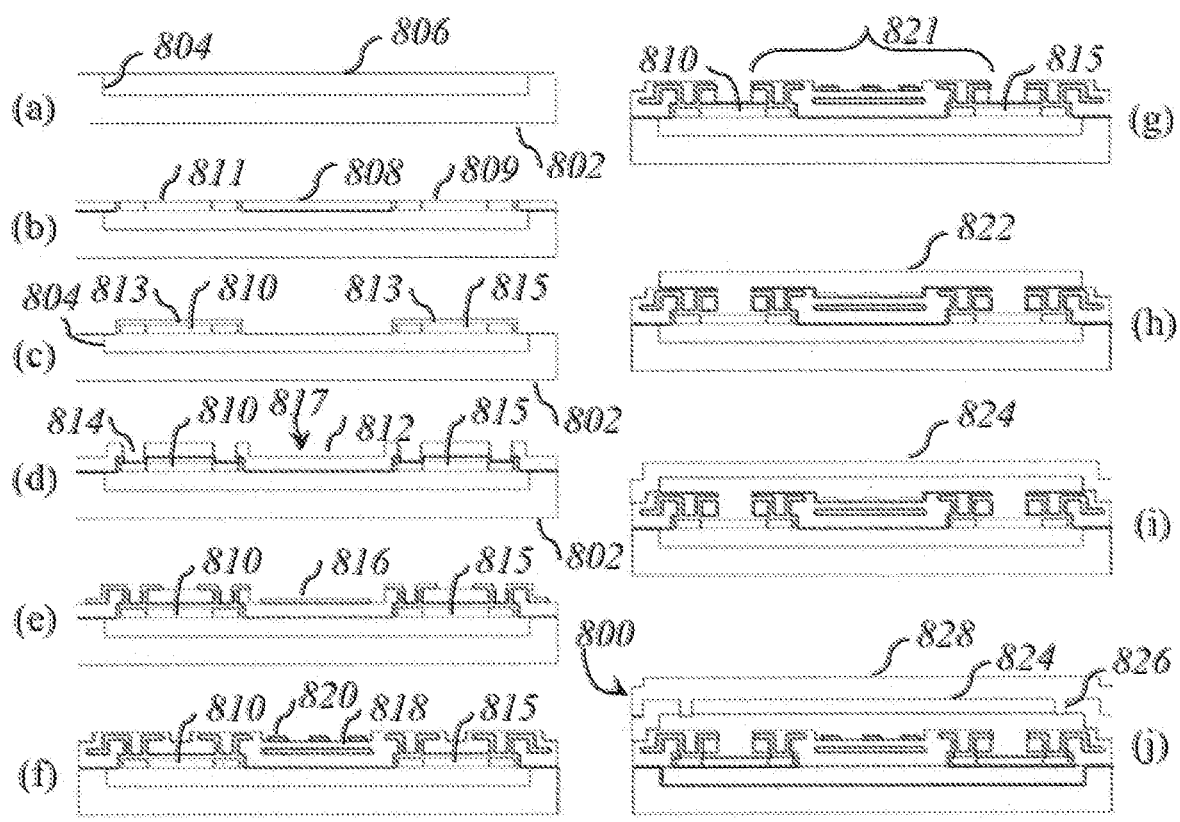
FIG. 9a) to j) show respective line drawings illustrating the process flow of fabricating the thermopile device of FIG. 8.

The process flow of fabricating the thermopile device 800 is described below in FIG. 9. The process begins with a Si wafer 802. A cavity 804 is first etched on the Si wafer 802 for 2 μm. A $SiO_2$ layer 806 (more than 2 μm) is deposited on the whole wafer 802 and then the $SiO_2$ 806 is planarized by chemical mechanical polishing (CMP), as shown in FIG. 9a). A Polysilicon layer 808 is deposited and then doped as N-type and P-type Polysilicon 809, 811, the area designed for electrical contact are further heavily doped to achieve a low contact resistance with metal, as shown in FIG. 9b). The Polysilicon layer 808 is etched with $SiO_2$ hard mask 813 to form the N-type and P-type arms 810, 815. The Polysilicon arms 810, 815 are only located within the perimeter of the $SiO_2$ cavity 804 without any physical connection with the Si substrate 802, as shown in FIG. 9c). $Al_2O_3$ 812 is deposited, this layer 812 serves as the insulation layer for the metal interconnection later. The $Al_2O_3$ layer 812 is also the physical connection between the arms 810, 815 of thermocouples and Si substrate 802, as well as the arms 810, 815 and metamaterial absorber, forming a carrier 817 for the metamaterial absorber structure. Vias 814 are opened on the $Al_2O_3$ layer 812 to allow electrical interconnection to form with the heavily doped Polysilicon 810, 815, as shown in FIG. 9d). Metal (Mo) 816 is deposited and etched. This metal layer 816 works as the interconnection between Polysilicon arms 810, 815 and also is the bottom layer of the metamaterial absorber structure, see FIG. 9e). Another layer of dielectric 818 and another layer of metal 820 is deposited and the metal layer 820 is etched to form the metamaterial pattern for the top layer of the metamaterial absorber structure, with a portion of the dielectric layer 818 forming the middle dielectric of the metamaterial absorber, as shown in FIG. 9f). The $Al_2O_3$ 818 is selectively removed above the Polysilicon arms 810, 815, and also forms the shape of the absorber 821, as shown in FIG. 9g). A thick layer of $SiO_2$ 822 is deposited and planarized. The $SiO_2$ 822 is etched and the $SiO_2$ 822 is left above the device, as shown in FIG. 9h). AlN 824 is deposited to seal the device, as shown in FIG. 9i). On the AlN layer 824, release holes 826 are etched. Vapor Hydrofluoric acid release is conducted to suspend the absorber 821 and arms 810, 815. The devices are again sealed with another layer of $SiO_2$ 828, as shown in FIG. 9j). Electrical contact pads (not shown) are opened and formed outside the encapsulation In the embodiments described above, a metamaterial layer is advantageously included to provide selective (i.e. narrow bandpass) emission/absorption for specific wavelengths. The metamaterial layer comprising a combination made of Mo—AlN—Mo used in the embodiments described above is additionally advantageous, promising low thermal stress and fast thermal response.

Figure 11:
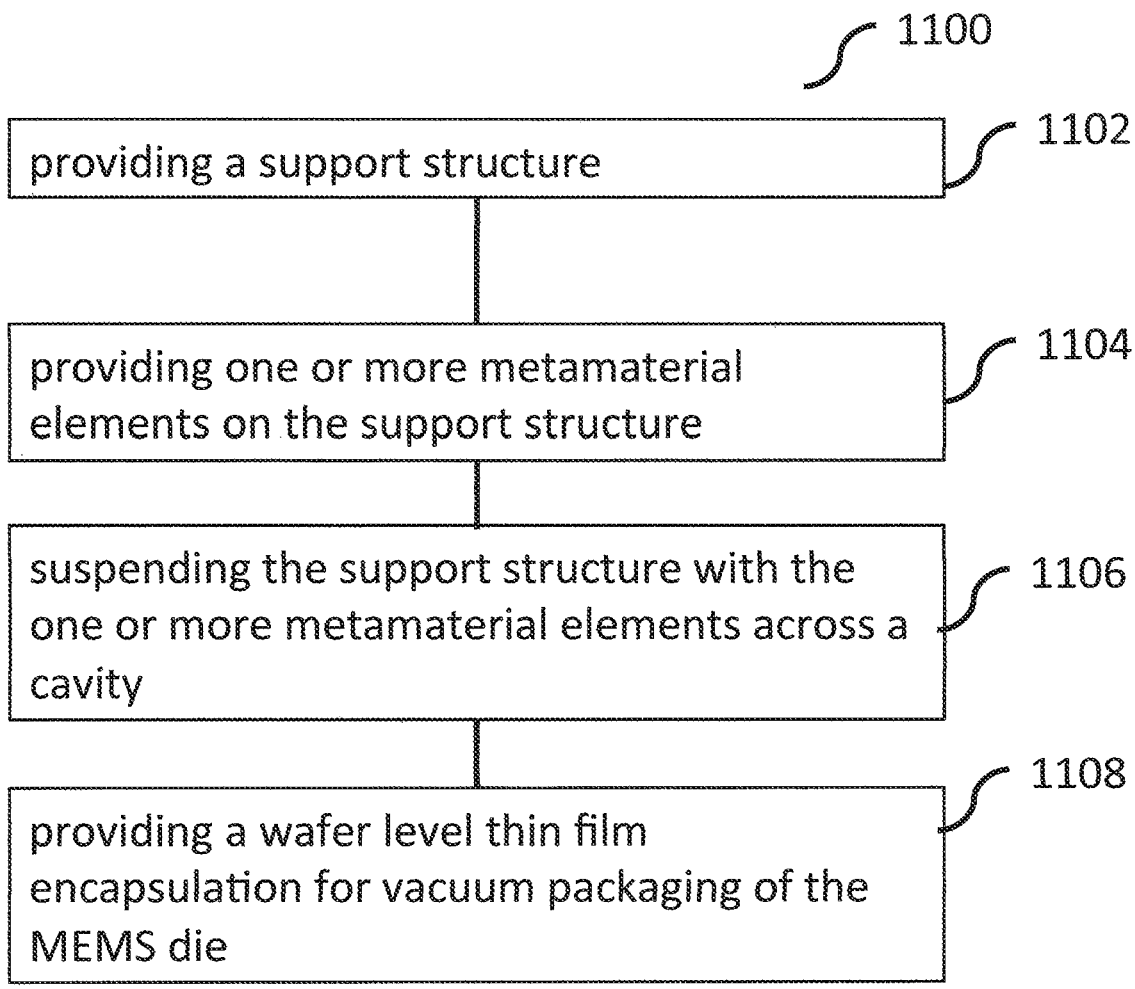
FIG. 11 shows a flow chart illustrating a method for fabricating a micro electro-mechanical system (MEMS) die for a heater or thermopile, according to one embodiment.

FIG. 11 shows a flow chart 1100 illustrating a method for fabricating a micro electro-mechanical system (MEMS) die for a heater or thermopile, according to one embodiment. At step 1102, a support structure is provided. At step 1104, one or more metamaterial elements are provided the support structure. At step 1006, the support structure with the one or more metamaterial elements is suspended across a cavity. At step 1008, a wafer level thin film encapsulation is provided for vacuum packaging of the MEMS die.

The may comprise forming the cavity by removal of a sacrificial material from a recess formed in a substrate made of a material different from the sacrificial material. The support structure may be formed within the perimeter of the cavity and the method further comprises forming a physical connection between the substrate and the support structure across a peripheral gap between the support structure and the substrate. The physical interconnection may comprise a metal interconnection to the support structure and an insulation layer for the metal interconnection.

Providing the wafer level thin film encapsulation may comprise using a complementary metal-oxide-semiconductor (CMOS) compatible process.

The MEMS die may be for the heater, and the one or more metamaterial elements may function as an emitter for one or more wavelengths. Providing the supporting structure may comprise forming heating wire and support arm portions of the support structure, wherein the metamaterial elements may be formed on the heating wire portion.

The MEMS structure may be for the thermopile, and the one or more metamaterial elements may function as an absorber for one or more wavelengths. Providing the supporting structure may comprise forming thermocouple and carrier portions of the support structure, wherein the metamaterial elements may be formed on the carrier portion. The thermocouple portion may surround the carrier portion.

In one embodiment, a micro electro-mechanical system (MEMS) die for a heater or thermopile is provided, the MEMS die comprising a support structure; one or more metamaterial elements on the support structure; the support structure with the one or more metamaterial elements across a cavity; and a wafer level thin film encapsulation for vacuum packaging of the MEMS die.

The cavity may be formed by removal of a sacrificial material from a recess formed in a substrate made of a material different from the sacrificial material. The support structure may be formed within the perimeter of the cavity and the MEMS die may further comprise forming a physical connection between the substrate and the support structure across a peripheral gap between the support structure and the substrate. The physical interconnection may comprise a metal interconnection to the support structure and an insulation layer for the metal interconnection.

The wafer level thin film encapsulation may be formed using a complementary metal-oxide-semiconductor (CMOS) compatible process.

The MEMS die may be for the heater, and the one or more metamaterial elements may function as an emitter for one or more wavelengths. The supporting structure may comprise heating wire and support arm portions, wherein the metamaterial elements may be formed on the heating wire portion.

The MEMS structure may be for the thermopile, and the one or more metamaterial elements function as an absorber for one or more wavelengths. The supporting structure may comprise thermocouple and carrier portions, wherein the metamaterial elements may be formed on the carrier portion. The thermocouple portion may surround the carrier portion.

Embodiments of the microheater device can have one or more of the following features and associated advantages:
- Dielectric-less supporting arms to reduce power consumption, eliminate the residual stress induced by the dielectric layer
- Cavity beneath the micro-heater to prevent over release to enhance performance and yield
- Metamaterial emitter surface coating for microheater to get wavelength selective emission
- Vacuum level encapsulation to enhance performance and largely reduce the fabrication cost.

Embodiments of the thermopile device can have one or more of the following features and associated advantages:
- Dielectric-less thermocouple which will increase output voltage and eliminate the residual stress induced by the dielectric layer in the released structure.
- Cavity beneath the thermopile to prevent over release, and there by enhances the device performance and fabrication yield
- Metamaterial absorber to provide selective absorption for specific wavelength
- Vacuum level encapsulation to enhance device performance and largely reduce the fabrication cost.

The commercial applications of embodiments of this aspect of the present Invention can include:
- Internet of Thing (IoT) applications
- Wearable and Smartphone systems
- Heating, ventilation and air conditioning (HVAC) systems
- Demand-controlled ventilation (DCV) systems
- Indoor air quality (IAQ) applications
- Non-dispersive infrared (NDIR) measurement of gas concentration
- Non-contact temperature measurement
- Semiconductor process monitor
- Distributed $CO_2$ sensing
- Green buildings
- Infrared spectroscopy
- Gases detection
- Hazardous-gas detection
- Material characterization
- Fire & Flame Detection
- Radiometers The various functions or processes disclosed herein may be described as data and/or instructions embodied in various computer-readable media, in terms of their behavioral, register transfer, logic component, transistor, layout geometries, and/or other characteristics. Computer-readable media in which such formatted data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof. Examples of transfers of such formatted data and/or instructions by carrier waves include, but are not limited to, transfers (uploads, downloads, e-mail, etc.) over the internet and/or other computer networks via one or more data transfer protocols (e.g., HTTP, FTP, SMTP, etc.). When received within a computer system via one or more computer-readable media, such data and/or instruction-based expressions of components and/or processes under the system described may be processed by a processing entity (e.g., one or more processors) within the computer system in conjunction with execution of one or more other computer programs.

Aspects of the systems and methods described herein may be implemented as functionality programmed into any of a variety of circuitry, including programmable logic devices (PLDs), such as field programmable gate arrays (FPGAs), programmable array logic (PAL) devices, electrically programmable logic and memory devices and standard cell-based devices, as well as application specific integrated circuits (ASICs). Some other possibilities for implementing aspects of the system include: microcontrollers with memory (such as electronically erasable programmable read only memory (EEPROM)), embedded microprocessors, firmware, software, etc. Furthermore, aspects of the system may be embodied in microprocessors having software-based circuit emulation, discrete logic (sequential and combinatorial), custom devices, fuzzy (neural) logic, quantum devices, and hybrids of any of the above device types. Of course the underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, etc.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above description of illustrated embodiments of the systems and methods is not intended to be exhaustive or to limit the systems and methods to the precise forms disclosed. While specific embodiments of, and examples for, the systems components and methods are described herein for illustrative purposes, various equivalent modifications are possible within the scope of the systems, components and methods, as those skilled in the relevant art will recognize. The teachings of the systems and methods provided herein can be applied to other processing systems and methods, not only for the systems and methods described above.

The elements and acts of the various embodiments described above can be combined to provide further embodiments. These and other changes can be made to the systems and methods in light of the above detailed description.

In general, in the following claims, the terms used should not be construed to limit the systems and methods to the specific embodiments disclosed in the specification and the claims, but should be construed to include all processing systems that operate under the claims. Accordingly, the systems and methods are not limited by the disclosure, but instead the scope of the systems and methods is to be determined entirely by the claims.

The invention claimed is:

1. A gas sensor comprising:
   a first micro electro-mechanical system (MEMS) die comprising a light source;
   a second MEMS die comprising a light detector;
   a sample chamber disposes in an optical path between the light source and the light detector; and
   a holder substrate;
   wherein the first and second MEMS dies are disposed on the holder substrate in a vertical orientation relative to the holder substrate, and with the sample chamber disposed laterally there between;
   wherein the sample chamber comprises a waveguide diffusion chamber, and
   wherein opposing open ends of the waveguide diffusion chamber function as diffusion apertures.

2. The gas sensor of claim 1, wherein the light detector comprises one or more conversion elements for converting a temperature change into an electrical signal and one or more first metamaterial elements thermally coupled to respective ones of the conversion elements, the first metamaterial elements configured for selective absorption at one or more wavelengths emitted by the light source and means for converting changes in the absorption at the one or more wavelengths into a variable electrical response.

3. The gas sensor of claim 1, further comprising vacuum level thin film encapsulations for the first and second dies, respectively, for thermal isolation of the light source and the light detector from a gas sample.

4. The gas sensor of claim 1, wherein the light source comprises one or more heater elements and one or more second metamaterial elements thermally coupled to respective ones of the heater elements, the second metamaterial elements configured for emission at the one or more wavelengths and/or further comprising a processing circuit with, at least, a source driver for driving the light source and an analogue interface coupled to the light detector, and preferably wherein the processing circuit is integrated on the holder substrate.

5. A method of manufacturing a gas sensor comprising the steps of:
   providing a first micro electro-mechanical system (MEMS) die comprising a light source;
   providing a second MEMS die comprising a light detector;
   providing a sample chamber disposed in an optical path between the light source and the light detector; and
   providing a holder substrate;
   wherein the first and second MEMS dies are disposed on the holder substrate in a vertical orientation relative to the holder substrate, and with the sample chamber disposed laterally there between;
   wherein the sample chamber comprises a waveguide diffusion chamber, and
   wherein opposing open ends of the waveguide diffusion chamber function as diffusion apertures.

6. The method of claim 5, wherein providing the light detector comprises providing one or more conversion elements for converting a temperature change into an electrical signal and thermally coupling one or more first metamaterial elements to respective ones of the conversion elements, the first metamaterial elements configured for selective absorption at one or more wavelengths emitted by the light source and means for converting changes in the absorption at the one or more wavelengths into a variable electrical response.

7. The method of claim 5, further comprising providing vacuum level thin film encapsulations for the first and second dies, respectively, for thermal isolation of the light source and the light detector from a gas sample.

8. The method of claim 5, wherein providing the light source comprises providing one or more heater elements and thermally coupling one or more second metamaterial elements to respective ones of the heater elements, the second metamaterial elements configured for emission at the one or more wavelengths, and/or further comprising providing a processing circuit with, at least, a source driver for driving the light source and an analogue interface coupled to the light detector, and preferably comprising integrating the processing circuit on the holder substrate.

* * * * *